US006867859B1

(12) United States Patent
Powell

(10) Patent No.: US 6,867,859 B1
(45) Date of Patent: Mar. 15, 2005

(54) INDUCTIVELY COUPLED PLASMA SPECTROMETER FOR PROCESS DIAGNOSTICS AND CONTROL

(75) Inventor: Gary Powell, Petaluma, CA (US)

(73) Assignee: Lightwind Corporation, San Francisco, CA (US)

( * ) Notice: Subject to any disclaimer, the term of this patent is extended or adjusted under 35 U.S.C. 154(b) by 591 days.

(21) Appl. No.: 09/631,271

(22) Filed: Aug. 2, 2000

Related U.S. Application Data

(60) Provisional application No. 60/146,877, filed on Aug. 3, 1999.

(51) Int. Cl.[7] .................................................. G01J 3/30
(52) U.S. Cl. ....................................................... 356/316
(58) Field of Search ......................................... 356/316

(56) References Cited

U.S. PATENT DOCUMENTS

| | | | | |
|---|---|---|---|---|
| 3,648,015 A | * | 3/1972 | Fairbairn ..................... 427/453 |
| 3,653,766 A | * | 4/1972 | Walters et al. ............... 356/313 |
| 3,958,883 A | * | 5/1976 | Turner ......................... 356/316 |
| 3,984,681 A | * | 10/1976 | Fletcher et al. ............. 250/290 |
| 4,147,431 A | | 4/1979 | Mann |
| 4,609,426 A | | 9/1986 | Ogawa |
| 4,629,887 A | * | 12/1986 | Bernier ........................ 356/316 |
| 4,847,792 A | | 7/1989 | Barna et al. |
| 4,857,136 A | | 8/1989 | Zajac |
| 4,859,277 A | | 8/1989 | Barna et al. |
| 5,066,125 A | * | 11/1991 | Rogers et al. ............... 356/316 |
| 5,180,949 A | * | 1/1993 | Durr ........................... 356/316 |
| 5,273,610 A | | 12/1993 | Thomas, II et al. |
| 5,326,975 A | | 7/1994 | Barna |
| 5,372,783 A | | 12/1994 | Lackie |
| 5,383,019 A | * | 1/1995 | Farrell et al. ............... 356/316 |
| 5,529,657 A | * | 6/1996 | Ishii ........................ 156/345.26 |
| 5,546,322 A | | 8/1996 | Gifford et al. |
| 5,671,045 A | | 9/1997 | Woskov et al. |
| 5,777,735 A | | 7/1998 | Reagen |
| 5,857,890 A | | 1/1999 | Ferran |
| 5,877,032 A | | 3/1999 | Guinn et al. |
| 5,949,193 A | | 9/1999 | Roine et al. |
| 5,963,336 A | | 10/1999 | McAndrew et al. |
| 5,986,747 A | * | 11/1999 | Moran ......................... 356/316 |
| 6,045,618 A | | 4/2000 | Raoux et al. |
| 6,046,796 A | | 4/2000 | Markle et al. |
| 6,068,783 A | | 5/2000 | Szetsen |
| 6,075,609 A | | 6/2000 | Tarkanic et al. |
| 6,101,971 A | * | 8/2000 | Denholm et al. ......... 118/723 E |
| 6,120,734 A | | 9/2000 | Lackie |
| 6,134,005 A | | 10/2000 | Smith, Jr. et al. |
| 6,333,269 B2 | * | 12/2001 | Naito et al. ................. 438/706 |
| 6,381,022 B1 | | 4/2002 | Zavracky |

FOREIGN PATENT DOCUMENTS

JP              58084431 A           5/1983

OTHER PUBLICATIONS

Danner et al. "Downstream Atomic Monitoring for Absolute Etch Rate Determinations" J. Electrochem. Soc: Solid–State Science and Technology Apr. 1983.

Lichtman Residual Gas Analysis: Past, Present and Future J. Vac. Sci. Technol. A 8 (3) May/Jun. 1990, 1990 American Vacuum Society.

* cited by examiner

Primary Examiner—John R. Lee
Assistant Examiner—Johnnie L Smith, II
(74) Attorney, Agent, or Firm—Ernest J. Beffel, Jr.; Haynes Beffel & Wolfeld LLP

(57) ABSTRACT

The present invention relates to an apparatus and method for forming a plasma in the exhaust line of a primary process reactor. The plasma is generated in an inductive source (5) to examine the chemical concentrations of the waste or exhaust gas in vacuum lines that are below atmospheric pressure. The optical radiation emitted by the plasma is analyzed by an optical spectrometer (9) and the resulting information is used to diagnose, monitor, or control operating states in the main vacuum vessel.

24 Claims, 4 Drawing Sheets

INDUCTIVELY COUPLED PLASMA SPECTROMETER FOR PROCESS DIAGNOSTICS AND CONTROL

CROSS-REFERENCE TO RELATED APPLICATIONS

This application claims the benefit of provisional Application No. 60/146,877, filed Aug. 3, 1999, entitled "Inductively Coupled Plasma Spectrometer for Process Diagnostics and Control".

BACKGROUND—FIELD OF INVENTION

This invention relates to the production of gas plasmas to be used for spectroscopic examinations, more particularly it is directed toward use with effluent gases from a primary process reactor.

BACKGROUND—DESCRIPTION OF PRIOR ART

The reliability and reproducibility of many industrial processes are improved by the use of sensor based analytical equipment. In semiconductor manufacturing many of those processes occur under vacuum. When the processes occur light may be emitted as a byproduct of the reactions. That light is a composition of wavelengths which are characteristic and unique to the reactions occurring. Measurement and an analysis of that light is accomplished with the use of optical spectrometers. Spectral analysis provides a means to control or terminate the chemical processes; or in other instances it may be used to diagnose, evaluate and optimize the operation of the manufacturing equipment. While this approach is valuable there are severe limitations in its applicability.

A typical embodiment of an optically sensor control is demonstrated in U.S. Pat. No. 4,263,088 to Gorin (1982) which discloses use of a photoconductive cell to monitor changes in light emission in a plasma processing chamber. Electrical changes in the photocell correspond to changes in light emission, or intensity, resulting from chemical state changes in the process. The electrical change is monitored by software to determine when to terminate the process. The process reactor may have a transparent window or a waveguide which allows transmission of the emitted light to a detector or sensor. A special optical fiber waveguide may be used. This approach has several serious disadvantages and limitations:

(a) Process control fluctuations or changes in the reactor introduce error in the accuracy of the analysis or determination of process state change. Any control change that affects the emitted light intensity of the process causes an electrical change in the photocell or detector which might be confused with the expected or predetermined change.

(b) The amount of light emission and therefore the sensitivity of the photocell or detector is dependent on the actual process condition. In normal operation a process is established which yields the desired chemical change in a material or substrate. Only the light that is a byproduct of the process may be used to monitor the process. Slow chemical reaction rates which characteristically produce less light are more difficult to monitor or analyze for change. Reaction rates in the primary reactor are not adjusted to increase light availability to the detect2or.

(c) Many optical processes occur which either emit insufficient light, or no light. No optical analysis or process monitoring can therefore occur.

U.S. Pat. No. 4,936,967 to Ikuhara (1990) discloses a method of determining endpoint with a wavelength specific detector on a plasma processing reactor. This technique also has the same shortcomings as the Gorin apparatus: the analysis is performed on the same reactor that is used to process materials or samples and is therefore limited to the specific performance of those processes and their control system. U.S. Pat. No. 4,312,732 to Degenkolb (1982) discloses a wavelength selectable optical detector which is used to control a reactor that etches photoresist. Photoresist is an organic material used as a mask in the transfer of images on materials. Degenkolb's device fails in the same manner as described in the Gorin patent.

To summarize this prior art, chemical processes are monitored directly by optical detectors, and chemical changes cause light changes detected by either individual photocells are arrays of photocells or other light sensitive devices. The performance of these devices is limited by the light byproduct of the process in use. They will not monitor gas compositional changes in processing environments where no light or insufficient light is emitted.

Other examples of prior art utilize inductively generated, non processing plasmas. An inductive plasma occurs when electrons having sufficient energy are transmitted through a coil or inductor into a gas at low pressure. That energy causes a decomposition or breakdown of the gas into ionized particles and energetic fragments. These plasmas emit light characteristic to the elements contained in the plasma. Inductive plasmas are generally used in analytical instruments as chemical ionization sources for spectral (optical or mass) analysis. These plasma apparatus operate at vessel pressures approximating 760 torr, normal atmospheric pressure. While these apparatus may be used for offline sampling of materials, their designs are not appropriate for continuous monitoring of waste effluent at below atmospheric pressure.

The different embodiments of these analytical instruments may be divided into several method categories, each with its own respective limitations:

(a) U.S. Pat. No. 4,501,965 to Douglas (1987), U.S. Pat. No. 4,551,609 to Falk (1985), U.S. Pat. No. 4,306,175 to Schlieicher (1981) discloses the requirement of double wall enclosure tubes where a the wall that creates the vacuum vessel contains the plasma, and a second wall acts either to confine gas cooling required for the tube, or to act as carrier gas inlet. A byproduct of a plasma reactions is heat which must be dissipated; one manner of dissipating heat is through gas flow. A carrier gas is a diluent that contains small amounts of the sample gas and is used to transport it into the plasma region. Both these approaches represent overly complicated mechanical embodiments of the art specific to operation and may be required for operation near or at atmospheric pressure.

(b) Power coupling or matching of power into a plasma generator is the use of electrical components to match the electrical characteristics of a plasma to its power supply. The appropriate choice enables the efficient transfer of electrical energy into the plasma. The electrical characteristics required to initiate a plasma are different from those required for its steady state operation. Dependent on the operating requirements of the plasma more complex methods of matching may be required. U.S. Pat. No. 4,306,176 to Schleicher (1981) demonstrates a movable graphite piece which is required for plasma ignition, and then removed during analysis. The igniter internal to the vacuum vessel is required to start an arc or plasma current. When the arc has been created the electrical impedance of the gases is lowered. U.S. Pat. No. 5,949,193 to Roine also uses an internal rod as an electrode for plasma ignition.

(c) A traditional technique used as a means of improving power coupling, ignitions, and gas breakdown is the use of a carrier gas. In a typical embodiment radio frequency power is used to the carrier gas. However, inefficiencies in power conveyed to the plasma require a carrier gas which is more easily ionized and can transfer energy to the plasma and species of interest through gas phase collision mechanisms. Besides acting as an energy transfer medium, the carrier gas may be required to function as a reactor coolant. A typical consequence of both these approaches is that they behave as chemical diluents: power transfer efficiency is lost in energizing that carrier gas. And, in many cases the carrier gas has its own characteristic spectra which may be superposed on the optical spectra under study. Optical emissions from the carrier gas can become background noise from which the signal of interest must be extracted. Examples of the use of a carrier gas mechanism are seen in U.S. Pat. No. 4,501,965 to Douglas (1987), U.S. Pat. No. 4,844,612 to Durr (1989), (d) Traditional designs restricted to high pressure, low gas flow operation. Suitable vacuum seals to prevent gas leaks are not included for operation below 500 mtorr. They are intended for small, less than 500 cc, gas samples.

(e) The inductive plasma apparatus previously mentioned are not designed for continuous operation in monitoring low pressure (below 100 torr) process reactor effluent and are not compatible in their current embodiments for such applications. Gas channels are small sizes which will not adequately transport continuous high gas flows.

SUMMARY

The present invention overcomes inadequacies of prior art which generally teach the use of optical or light emission and monitoring which is directly connected through windows and light conductive cables to the processing reactor. Or, in the case of inductive plasmas used for chemical analysis, their designs are specific to operation at pressure above 500 mtorr. The designs also require complicated plasma ignition hardware internal to the plasma chamber.

This present invention utilizes an inductive plasma which ionizes gas effluent at pressures below 100 mtorr to above 10 torr. The plasma is used as an ionization and light source for spectroscopic (optical or mass) studies of chemical changes in the reactor as seen in its gas effluent. Those changes can be recorded for documentation of stable processes, control, or process termination.

OBJECTS AND ADVANTAGES

Accordingly, the objects and advantages of the present invention are:

(a) to provide a monitor, control or analysis tool that is less susceptible to control perturbations or errors in the primary process vessel, (b) to provide a remote plasma whose light intensity can be varied independently of the process reactor thereby giving an additional means to improve detector sensitivity (c) to provide a method where monitoring and analysis can be used to detect chemical abundances when low reaction rates, or no reaction exists to emit sufficient light.

(d) to provide a simpler reactor design that does not require either double wall tubing, or a special inlet for swirling or mixing of carrier or sample gas (e) to provide an inductive source that is consistent with operating pressures below 20 torr.

(f) to provide an apparatus which will sustain an uninterrupted plasma to be used in gas analysis (g) to provide an inductive plasma source that does not require a carrier gas for cooling, or a special gas for plasma ignition (h) to provide an inductive plasma source that will ionize or decompose a variety of gas mixes without energy loss to a carrier gas or diluent (i) to provide a plasma reactor and matching device that does not require an internal electrode, or constrict flow of process effluent, (j) to provide a combination of plasma source and detector system that monitors/analyzes gas state change as it occurs.

Further objects and advantages of my invention will become apparent from a consideration of the drawings and ensuing description.

REFERENCE NUMERAL IN DRAWINGS

Figure 1:
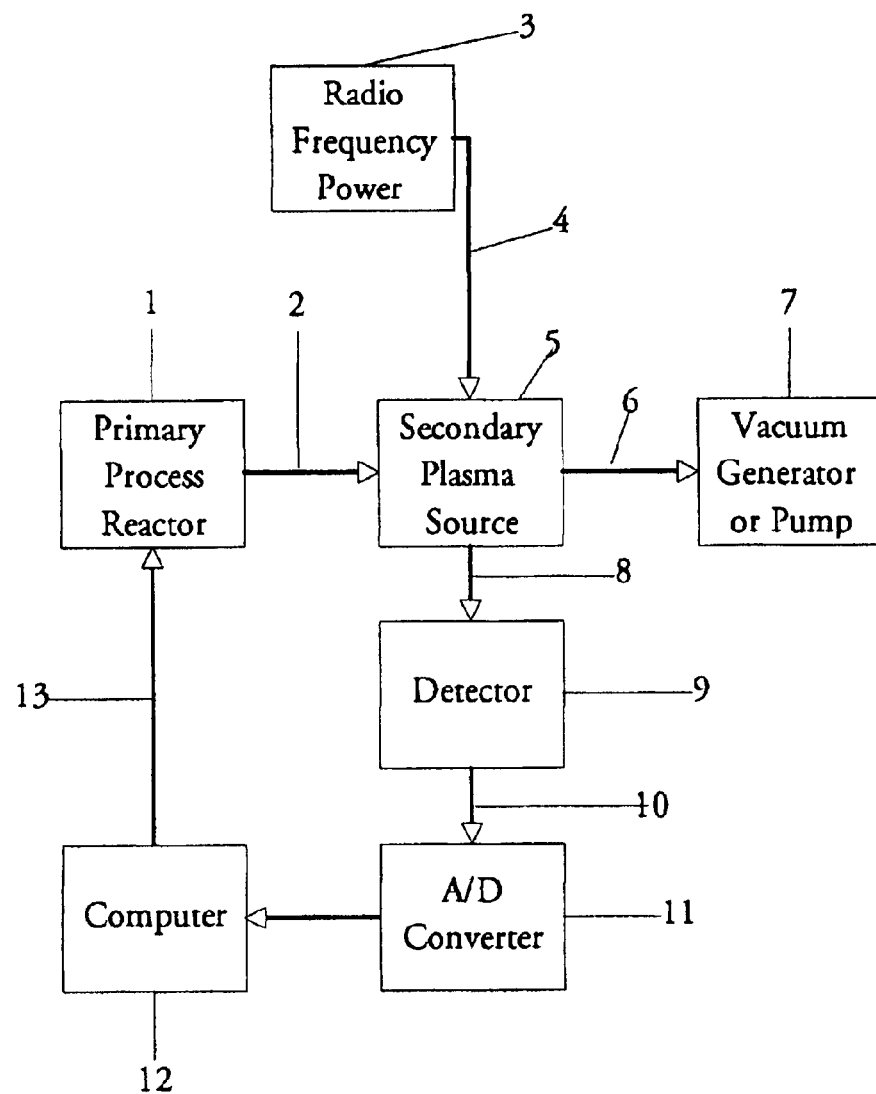
FIG. 1 is a schematic diagram showing all the major elements of the invention.

1 Process reactor
2 Vacuum line from reactor to invention
3 R.F. Power supply
4 R.F. cable
5 Secondary plasma source
6 Vacuum line to vacuum pump
7 Vacuum pump or generator
8 Fiber optic cable to detector
9 Optical detector
10 Cable from detector to computer
11 Analog/Digital converter
12 Computer
13 Communication cable
14 Detector array, CCD or photocell
15 Diffraction grating
16 Focusing/collecting lens/slit
17 O ring seal
18 Optical/vacuum blank off
19 O ring seal
20 Vacuum T
21 O ring seal
22 R.F. bulkhead fitting and cable interface
23 Capacitor
24 Ignition ring
25 Inductor coil
26 Hold down screw for skin or covering 27 Source output cap
28 O ring seal
29 Vacuum output to pump
30 Plasma tube
31 R.F. connector wire
32 Skin or covering
34 Bolt
35 Source input cap
36 Vacuum input from reactor
37 Sapphire window
38 Fiber optic connector
39 Screw
41 Matching network resistor
42 Matching network capacitor
44 Skin or outer covering
45 Source input cap
46 O ring
47 Bolt
49 Optical adaptor
51 Vacuum T
52 Plasma Tube
53 O ring seal
54 R.F. connector wire
58 Support bracket
60 Ignition ring
61 Ground wire Detailed Description—FIGS. 1, 2, 2A, and 2B—
Preferred Embodiment Referring now to the drawings, FIG. 1 shows a schematic overview of a secondary plasma source or generator 5 which has been inserted in a vacuum exhaust line 2 of a primary process reactor 1. The output of the plasma source 5 is connected to an exhaust line 6 which is connected to a vacuum pump or generator 7. A radio frequency power supply 3 provides sufficient energy at 13.56 megahertz through a cable 4 to create a plasma in the source 5. A fiber optic cable 8 transmits emitted light from the plasma to a light detector 9. The light detector converts photonic energy into a packet of analog signals which are transmitted over a communication cable 10 to an analog/digital converter 11 and is then processed by a computer 12. The computer analyzes, monitors, and records time based data from the optical detector 9 and the appropriate information is sent over a communication cable 13 to the main processing reactor 1 where the information may be utilized.

Figure 2:
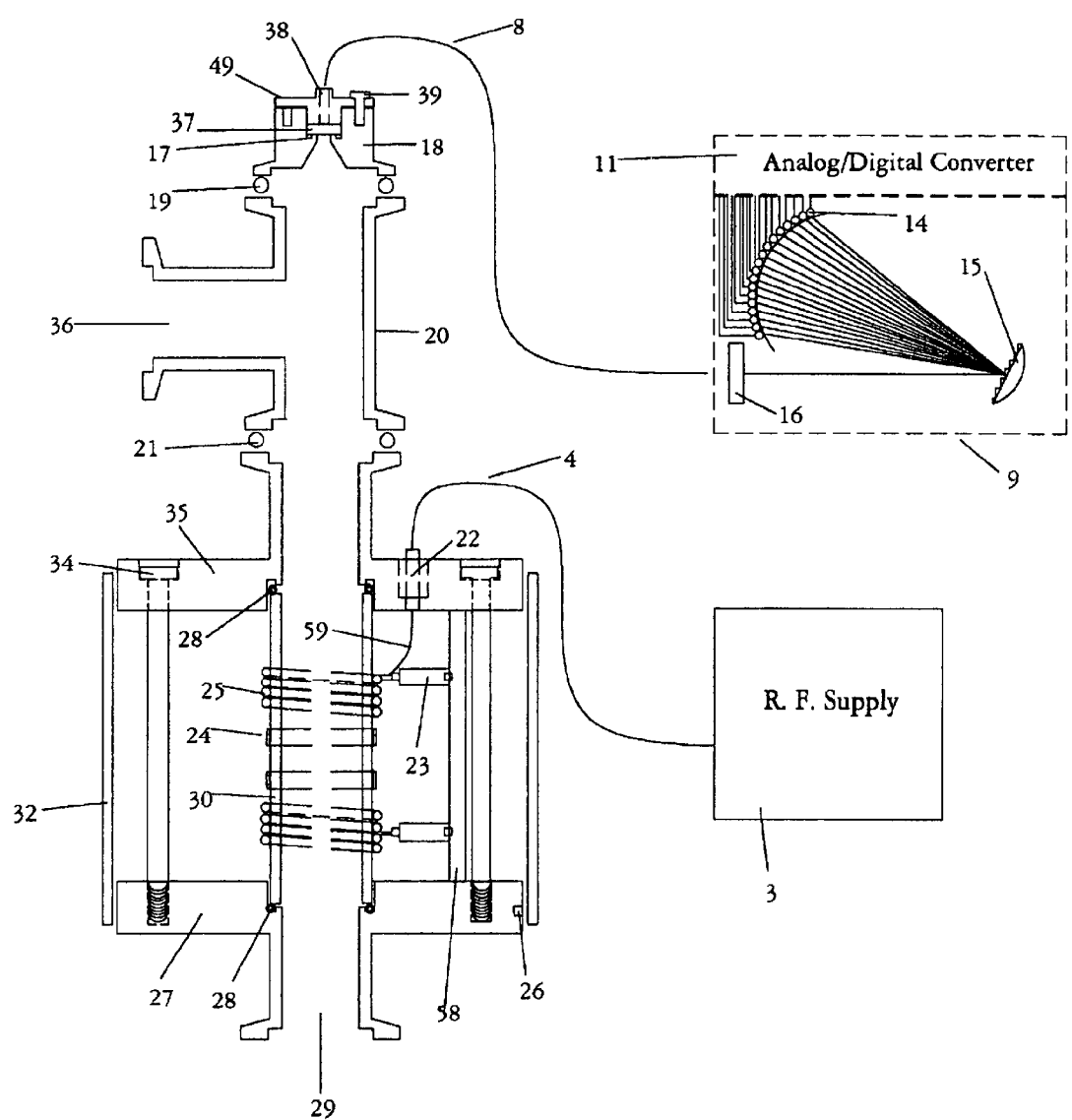
FIG. 2 is a more detailed view of the specific plasma source showing the relationship of the vacuum vessel to the radio frequency supply and optical sensor.
Figure 2A:
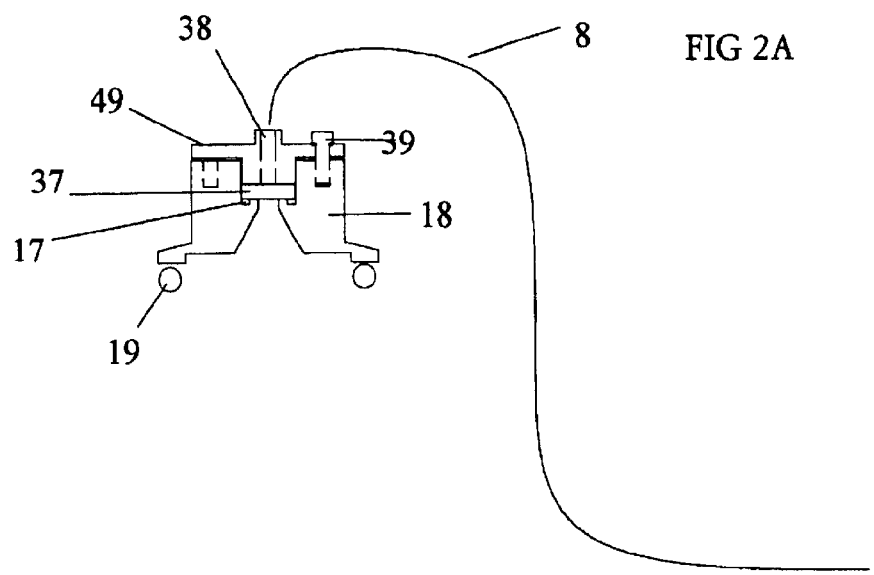
FIG. 2A is an enlarged view of the optical window to the plasma

FIG. 2 shows a more detailed cross section of the plasma source 5 which provides light as part of this invention. Vacuum enters the apparatus at 36 from the host processing reactor 1 and is transported through a vacuum "T" 20 into a source input cap 35. After passing through the cap 35 gas then flows through a ceramic plasma tube 30 into a source vacuum output 27, finally exiting the vessel at 29 through an output flange into the exhaust line 6. The invention isolates vacuum from atmosphere with a compressible o ring 21 between vacuum "T" 20 and source input cap 35. Another o ring 19, seals an optical vacuum blank off 18 to the vacuum T 20. A group of screws 39 compress an optical adaptor or connector 49 against a sapphire window 37 which in turn compresses o ring 17. A bolt 34 pulls the source input cap 35 against an o ring 28 sealing the gas input of a plasma tube 30. The output side of plasma tube 30 is also forced against a source vacuum output 27 which compresses o ring 28. The optical blank off 18 seals the vacuum in the system against atmosphere an provides a housing for the sapphire window 37 which has an opening to maximize the capture of light axially transmitted through vacuum tube 20 from plasma tube 30. Optical adaptor 49 both helps seal the window 37 as well as mechanically supports a fiber optic connector 38 which provides a quick connection to a fiber optic cable 8. Fiber optic cable 8 transmits light emission from the plasma to an detector 9. Light emerging from the cable 8 enters the detector 9 through a lens 16 which focuses it on a diffraction grating 15. The grating 15 separates the light into discrete wavelengths which are broadcast in an orderly fashion across a detector array 14. The array 14 converts photonic energy into electrical energy in the form of analog signals proportional to the intensity of the discrete wavelengths.

The secondary plasma source which is downstream is powered by a radio frequency power supply 3 which broadcasts at 13.56 megahertz into a power cable and then into an r.f. bulkhead connector 22. Connector 22 couples power into an electrical circuit through cable 31. That energy passes through a capacitor 23 into a coil 25 and a pair of ignition rings 24. This network generates an electrical discharge in plasma tube 30.

Figure 2B:
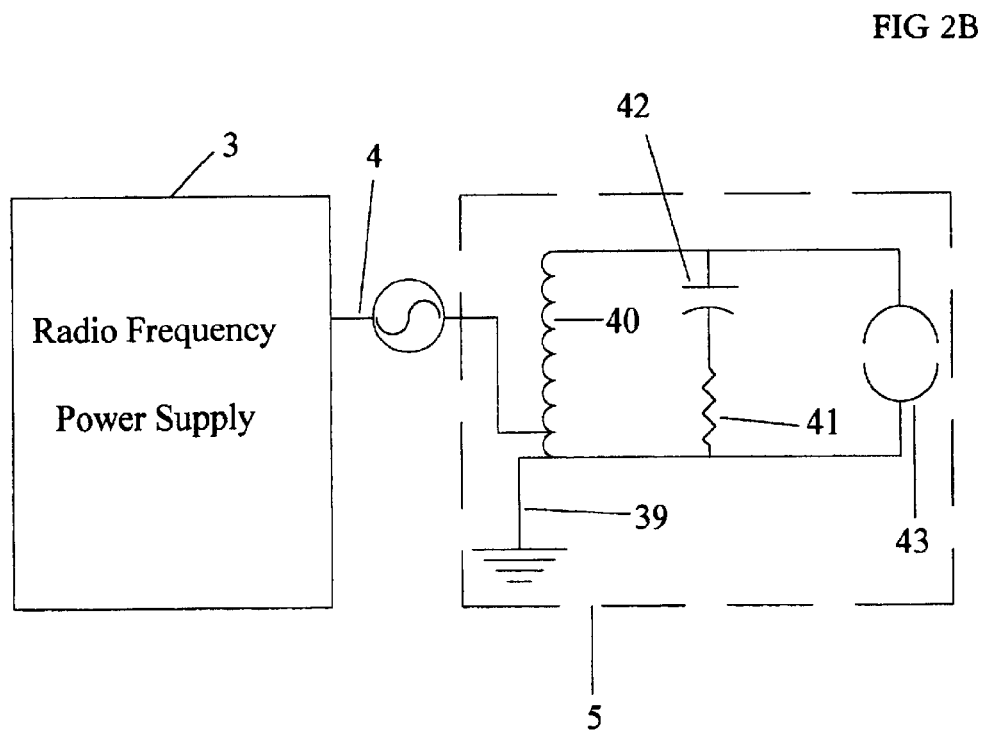
FIG. 2B is a schematic view of the radio frequency power supply and its power transfer section.

FIG. 2B shows an electrical schematic of the power transfer from connector 31 into the plasma. Energy enters a circuit comprised of a coil or inductor 25, a capacitor 42, a resistor 41 and two ignition rings 24 which function as a capacitor.

Figure 3:
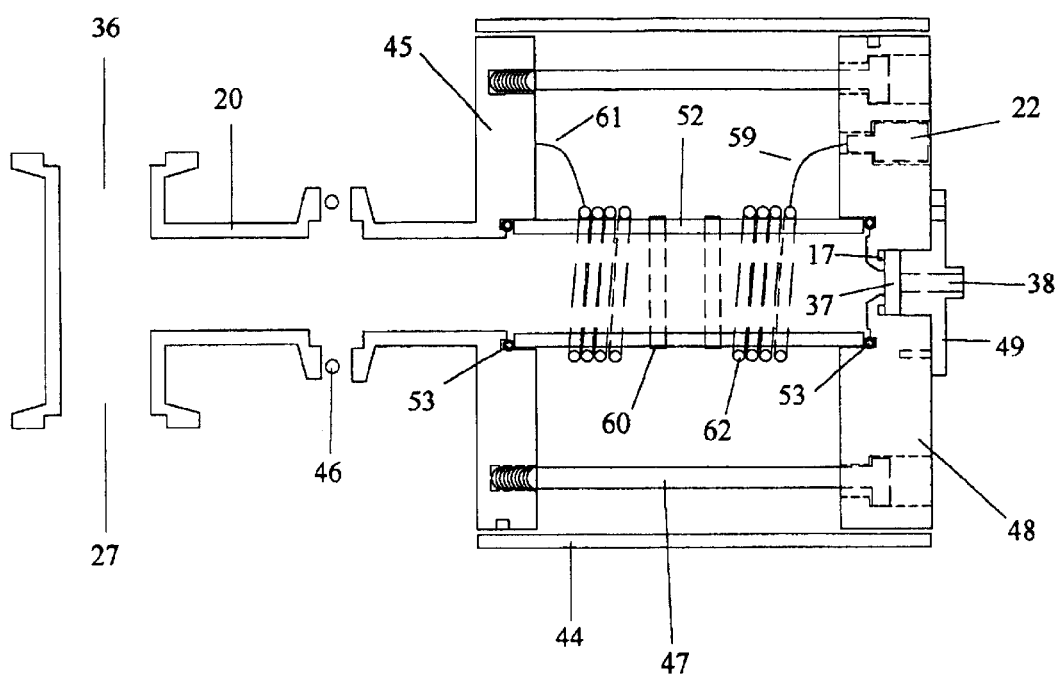
FIG. 3 is an enlarged view of an alternate configuration for the plasma source

FIG. 3—Additional Embodiments

An additional embodiment of the secondary plasma source is shown in FIG. 3. Where in FIG. 2, effluent from process reactor 1 passes through the downstream secondary plasma source, in FIG. 3 the effluent passes near the plasma source entering a vacuum "T" 20 through an opening 36 and exits through an opening 27. The "T" is sealed to a source input or flange 45 with an o ring 46. The input 45 is pulled toward a closed source flange 48 by a series of bolts 47. The input 45 compresses o ring 53 against plasma tube 52 which in turn compresses o ring 53 against the closed source flange 48. Plasma tube 52 both forms a wall of the vacuum vessel as well as supporting an inductor 62 and a pair of ignition rings 60. Power passes through the closed source flange 48 via an electrical bulkhead fitting 22 into the coils by connector 54 and is removed by a connector 61. Refer to FIG. 2B for the electrical schematic of the circuit. The plasma generated in tube 52 emits photonic energy which is transmitted through a sapphire window 37. A set of screws 38 force an optical adaptor flange 48 against the window 37 and therefore seal by compressing o ring 17.

Advantages

From the description above, a number of advantages of this apparatus become evident:

(a) A secondary plasma which decomposes process effluent can be used as part of an analysis system that is less susceptible to control perturbations or errors in the primary process vessel.
(b) Light intensity in the remote plasma can be varied independently of process changes in the primary reactor thereby giving an additional means to improve detector sensitivity
(c) A means of analyzing gases is provided when low reaction rates, or no reaction exists to in the primary processing reactor.
(d) Reactor designs provided in previous art are more complex and not appropriate for continuous vacuum operation.
(e) A means to both analyze and monitor gases for process and system control and diagnosis is provided across a wide range of process reactor operating states.

Operation—FIGS. 1, 2, 2A, 2B

During normal operation a process reactor 1 will have gas flowing in it with or without a process occurring. That gas flows through vacuum line 2 into and through the secondary plasma source 5. This effluent is a continual gas change exhibiting both bulk gas flow and diffusive gas flow; its content reflects the chemical profile of the main reactor. When there is an interest in the chemical content of the gas from the primary reactor a radio frequency generator or power supply 3 is turned on, that is, energy at a frequency of 13.56 megahertz is transmitted from it through a cable 4 to the secondary plasma source 5. A plasma is generated in the plasma tube 30. To improve power transfer efficiency a matching network is added to the source. Since the impedance of the gases before ignition or initiation of plasma is different than after ignition two bands 24 are used to capacitively ignite the plasma. The capacitors charge to a sufficient voltage to break down the gas in the plasma tube 30. When ignition occurs the impedance changes and power transfer occurs through the coils or inductor 25. A capacitor 42 is used to adjust the reactance of the circuit; power is shunted through resistor 41 to ground. This combination of passive components broadens the effective impedance range that power can efficiently be coupled in the plasma. When a plasma is initiated its volume changes as a function of the r.f. power input from the power supply 3. As the power is increased the gas breakdown and ion generation increase with a resulting increase in light emission. Applied power which drives the secondary plasma can be varied independently of control changes in the primary process reactor. A sapphire window 37 transmits light from approximately 200 nm. into the near infrared region as well as provides a wall that forms a vacuum seal. That window is placed so that the cylindrical volume filled by the plasma can be observed. The optical vacuum blank off 18 is shaped to optimize light capture into a fiber optic bundle 8. Light is transmitted through the light conductive bundle into a light detector 9. A focusing lens 16 optimizes the light transfer from the fiber cable into the detector 9 and is displayed on a diffraction grating 15 where it is decomposed into specific wavelengths and measured by a photocell or charge coupled device, CCD array 14. The array converts photonic energy into analog signals that are proportional to the intensity of the incident light. The analog signal is conveyed by a cable 10 to an analog to digital converter 11. The digitized information is then processed in a computer 12. A computer program analyzes the information and monitors the optical input for changes. That data is used to: terminate processes operating out of accepted error bounds, to terminate completed processes, to provide feedback for realtime control, and to record normal process performance for specific steady state manufacturing processes.

Operation—FIG. 3

The alternate embodiments shown utilizes the same functional components illustrated in FIG. 3 However the plasma source 5 has several significant modifications. The vacuum "T" 20 is oriented so that the bulk gas flow is from inlet 36 to outlet 27. There is no bulk gas flow into the plasma source 3. A closed source flange 48 seals the end of the vessel. Sample or gas change in the tube 52 is accomplished by normal gas diffusive processes which occur rapidly. This configuration has the benefit of simpler attachment to existing vacuum lines. Because the optical window 37 is mounted directly on the source, this apparatus does not require use of a vacuum T 20, but can instead be mounted on any compatible flange.

Conclusion, Ramifications, and Scope of Invention

Accordingly, the reader will see that the secondary plasma of this invention can be used to provide a remote control and analysis tool that is less affected by control error in a processing reactor. It also provides a remote plasma whose light intensity can be changed independent of the light emitted in the process reactor. Analysis, or monitoring can be optimized for sensitivity. A direct benefit of this capability is that process analysis can be accomplished where a process in the primary reactor has either a low reaction rate, or no reaction exists to emit sufficient light. This design utilizes a passive power matching network that efficiently couples r.f. power into a plasma over wide ranges of pressure and gas flow. The remote plasma source does not require complicated gas injection, gases other that the actual process gases, and can be used for realtime continuous state monitoring.

Furthermore, this apparatus has other advantages:

the secondary plasma source can be used to analyze unprocessed gases in the primary vacuum vessel and can continuously monitor for air leaks in that reactor this apparatus can be used for helium leak detection of the primary process reactor Although the description above contains many specificities, these should not be construed as limiting the scope of the invention but as merely providing illustrations of some of the presently preferred embodiments of this invention. For example:

the optical detector could be an individual photocell, the optical detector could have different lens and mirror arrangements, the secondary plasma source be placed downstream of a turbo pump, the optical detector could be replaced with a mass detector attached to the optical vacuum blank off or the closed source flange;

this apparatus could be powered by energy at a different frequency than 13.56 megahertz a detector sensitive to wavelengths longer than 1000 nm, might be used, information from this invention could act as a sensor for feedback and continuous control of a specific control element in the primary process reactor.

What is claimed is:

1. A plasma analysis device for analyzing a gaseous sample within a plasma chamber, including:

a plasma chamber;

an exhaust gas feed gaseously coupled to the plasma chamber;

a radio frequency power oscillator, disposed outside the plasma chamber, electromagnetically coupled to a space within the chamber;

an optical window into the plasma chamber;

a spectral analyzer comprising a grating and a detector array, optically coupled to the optical window.

2. The device of claim 1, wherein the plasma chamber is dedicated to generation of plasma light emissions for spectral analysis.

3. The device of claim 1, wherein the gaseous coupling allows diffusion of gas from the exhaust gas feed to the plasma chamber.

4. The device of claim 1, wherein the gaseous coupling allows flow of gas from the exhaust gas feed into the plasma chamber.

5. The device of claim 1, wherein the chamber operates at a gas pressure of 100 mtorr to 10 torr.

6. The device of claim 1, wherein the radio frequency power oscillator is adjustable to vary plasma light intensity, independent of any process upstream of the exhaust gas feed.

7. The device of claim 3, wherein the radio frequency power oscillator is adjustable to vary plasma light intensity, independent of any control changes to a process upstream of the channel.

8. The device of claim 1, wherein the optical window comprises sapphire.

9. The device of claim 6, wherein the optical window comprises sapphire.

10. The device of claim 7, wherein the optical window comprises sapphire.

11. The device of claim 1, wherein the optical window transmits light from approximately 200 nm to near infrared.

12. The device of claim 6, wherein the optical window transmits light from approximately 200 nm to near infrared.

13. The device of claim 7, wherein the optical window transmits light from approximately 200 nm to near infrared.

14. The device of claim 1, wherein optical coupling of the spectral analyzer and the optical window comprises a lens and light guide.

15. The device of claim 1, wherein the radio frequency power oscillator comprises a single resonant circuit including at least one induction coil and one or more tuning capacitors, and the induction coil and the tuning capacitors are in parallel.

16. The device of claim 1, wherein the radio frequency power oscillator matches impedance with the gas before and after ignition of the gas to a plasma state.

17. The device of claim 1, wherein ignition of the gas to a plasma state does not require any electrodes internal to the plasma chamber.

18. The device of claim 16, wherein ignition of the gas to a plasma state does not require any electrodes internal to the plasma chamber.

19. The device of claim 1, further including:

a computer, electronically coupled to the detector array; and logic and resources to monitor the detector array for signal changes.

20. The device of claim 19, wherein the logic and resources generate a control signal, further including:

process equipment gaseously coupled to the exhaust gas feed; and process control equipment, operatively connected to the process equipment, in communication with the logic and resources.

21. The device of claim 20, wherein the logic and resources generate a process end signal when a process is out of bounds.

22. The device of claim 20, wherein the logic and resources generate a process end signal when a process is complete.

23. The device of claim 20, wherein the logic and resources generate a process initiate signal.

24. The device of claim 19, wherein the logic and resources record operating conditions.

* * * * *